United States Patent [19]

Turi

[11] Patent Number: 5,312,341
[45] Date of Patent: May 17, 1994

[54] RETAINING APPARATUS AND PROCEDURE FOR TRANSSEPTAL CATHETERIZATION

[75] Inventor: Zoltan Turi, West Bloomfield, Mich.

[73] Assignee: Wayne State University, Detroit, Mich.

[21] Appl. No.: 930,340

[22] Filed: Aug. 14, 1992

[51] Int. Cl.$^5$ .......................................... A61M 25/00
[52] U.S. Cl. ........................................ 604/96; 600/16;
606/194; 128/898; 604/280
[58] Field of Search ................................. 604/96–103,
604/284, 280; 606/192, 194, 107–109;
600/16–18; 128/898

[56] References Cited

U.S. PATENT DOCUMENTS

| | | | |
|---|---|---|---|
| 3,833,003 | 9/1974 | Taricco | 604/96 |
| 4,985,014 | 1/1991 | Orejola | 600/16 |
| 5,030,199 | 7/1991 | Barwick et al. | 604/96 |
| 5,042,976 | 8/1991 | Ishitsu et al. | 604/96 |
| 5,073,166 | 12/1991 | Parks et al. | 604/105 |
| 5,112,310 | 5/1992 | Grobe | 604/96 |

OTHER PUBLICATIONS

C. Cope, "Technique for Transseptal Catheterization of the Left Atrium" J. Thoracic Surg., Apr. 1959, pp. 482 et seq.

E. Brockenbrough et al., "New Technic for Left Ventricular Angiocardiography & Transseptal Left Heart Catheterization" Am. Jo. of Cardiology, Dec. 1960, pp. 1062 et seq.

K. Kotoda et al., "Transseptal Left-Heart Catheterization w/Swan-Ganz Flow-Directed Catheter" Am. Heart J., Mar. 1983, pp. 436 et seq.

C. Mullin, "Transseptal Left Heart Catheterization: Experience with New Technique . . . " Pediatric Cardiology, vol. 4, No. 3, 1983, pp. 239 et seq.

N. Bridges et al., "Transcatheter Closure of Large Patent Ductus Arteriosus with the Clamshell Septal Umbrella", J. Am. Coll. Cardiology, vol. 18, No. 5, Nov. 1, 1991, p. 1297.

Photograph of Retrieval Basket Catheter.

*Primary Examiner*—C. Fred Rosenbaum
*Assistant Examiner*—Chalin Smith
*Attorney, Agent, or Firm*—Brooks & Kushman

[57] ABSTRACT

The invention comprises retaining apparatus for transseptal catheterization and a procedure for the use of same. The retaining apparatus is a selectively deployable retaining means disposed at or proximal to the tip of a transseptal catheter or sheath which is placed across a septum, such as the interatrial septum, into the left atrium. The retaining means is configured to cooperate with the distal portion of the sheath to present a uniform cylindrical circumferential periphery when the retaining means is undeployed and to present a shape generally transverse to the longitudinal axis of the sheath when deployed. In a preferred embodiment, the retaining means is a retaining balloon which, upon inflation, presents a relatively flat, disk-like shape to comprise a physical barrier preventing inadvertent retraction of the distal tip of the sheath from the left atrium during subsequent portions of the catheterization procedure. The transseptal catheterization procedure includes the steps of placing the distal tip of the transseptal sheath across a septum, deploying the retaining means for retaining the distal tip within the left atrium, completing the transseptal portion of the catheterization procedure, retracting the selectively deployable retaining means, withdrawing the distal tip from the septum and completing the procedure.

24 Claims, 2 Drawing Sheets

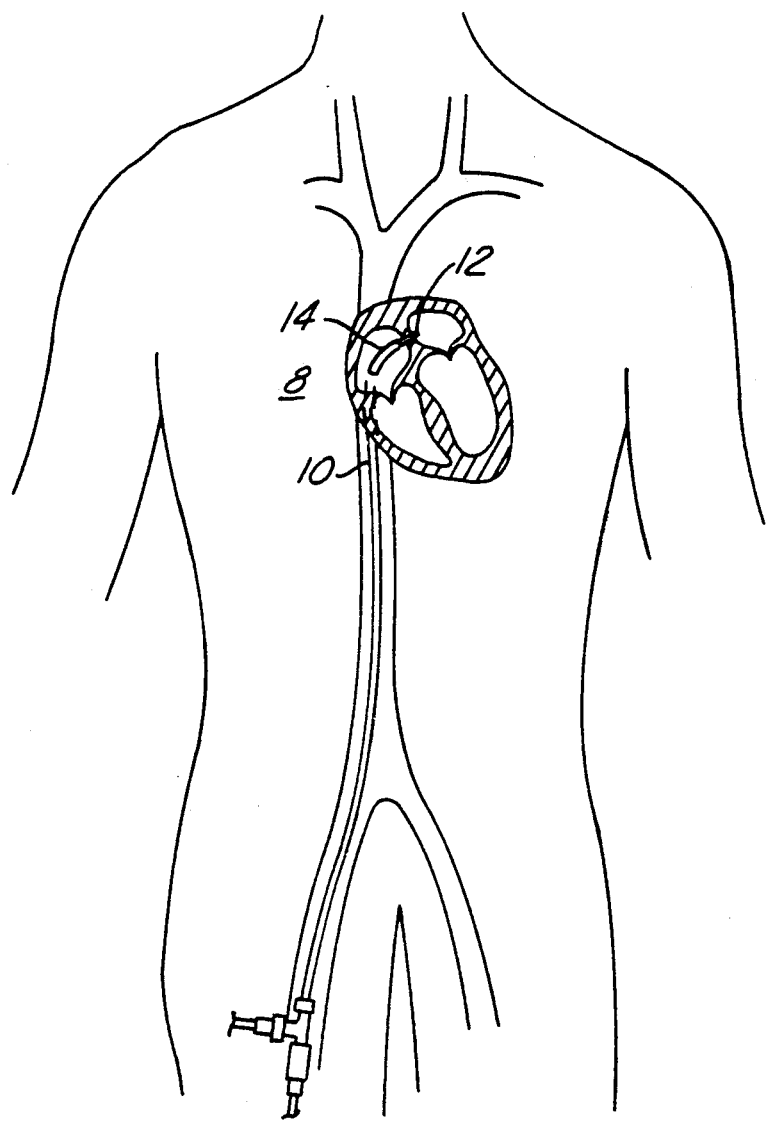
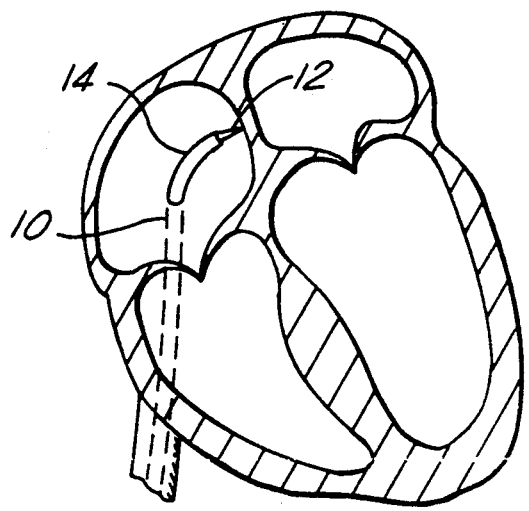
fig-1
fig-2a

RETAINING APPARATUS AND PROCEDURE FOR TRANSSEPTAL CATHETERIZATION

TECHNICAL FIELD

This invention relates generally to the field of catheterization, such as catheterization of the heart, and more particularly to transseptal catheterization.

BACKGROUND ART

Catheterization of the human heart, as for angioplasty and other cardiac procedures, continues to be used with ever-increasing frequency. Typically, the approach to the right atrium and right ventricle of the heart is accomplished by access through one of the femoral veins, and most commonly the right femoral vein. Presently, access to the left ventricle is typically accomplished by retrograde aortic approach.

The most difficult chamber of the heart to access with a catheter is the left atrium. Access to the left atrium through the pulmonary artery is not possible. Approaches from the left ventricle are difficult, may cause arrhythmias and may present difficulty in obtaining stable catheter positioning. Accordingly, the presently preferred method of accessing the left atrium is through a transseptal approach, that is, catheterization of the right atrium with subsequent penetration of the interatrial septum.

There are some risks attendant to transseptal catheterization, which are risks in addition to those associated with normal heart catheterization. The primary additional risk is that associated with inaccurate identification and localization of the atrial septum. Of course, unknowing, improper placement of the catheter tip prior to the transseptal puncture presents the risk of puncture of tissue other than the interatrial septum. For this reason, catheterization is accompanied by fluoroscopy or other visualizing techniques to assist in properly locating the catheter tip in relation to the septum, in a manner described in detail below.

Generally, the objectives of left atrial access are both diagnostic and therapeutic. One diagnostic use is pressure measurement in the left atrium. In the setting of an obstructed mitral valve (mitral stenosis), left atrial access allows a determination of the pressure difference between the left atrium and left ventricle. Left atrial access also allows entry into the left ventricle through the mitral valve. This is desirable when an artificial aortic valve is in place. The recent advent of aortic valve replacement with mechanical artificial valves, and the increase in the aged population and growing longevity of that population subsequent to aortic valve replacement, brings a greater need to evaluate the late stage functionality of such artificial valves.

Diagnostic measurement of the left ventricular pressures are, therefore, desirable to allow evaluation of mechanical artificial aortic valves post-replacement. It is unsafe to cross these mechanical artificial valves retrograde from the aorta; therefore, access to the left ventricle by the antegrade route using a transseptal puncture is the preferred approach. Once a catheter has been placed in the left atrium using the transseptal approach, access to the left ventricle can be gained by advancing catheters across the mitral valve.

It may be noted that where the mitral or aortic valves have been replaced with a mechanical artificial prothesis, retrograde access to the left atrium is generally viewed to be associated with unacceptably high risk. Of course, there are many diagnostic indications for left atrial pressure measurements in addition to evaluation of functionality of artificial mitral valves. Other diagnostic indications for accessing the left ventricle via the antegrade transseptal approach include aortic stenosis, when a cardiologist is unable to pass a catheter retrograde into the left ventricle, and some disease states where the antegrade approach is considered preferable, such as subaortic obstruction.

Presently, the therapeutic objectives of left atrial access are primarily two-fold. The first is mitral valvuloplasty which represents an alternative to surgical procedures to relieve obstruction of the mitral valve. The second therapeutic objective is for electrophysiological intervention in the left atrium. This procedure, radiofrequency ablation, is relatively new. The usage of this technique is in a growth trend.

Radiofrequency ablation involves the placement of a radiofrequency generating device through a catheter, into various locations of the heart to eradicate inappropriate electrical pathways affecting the heart function. When these locations are in the left atrium, the catheter through which the radiofrequency generator is placed typically is itself placed with transseptal catheterization.

For all of these objectives of left atrial access a sheath is typically introduced into the left atrium through which appropriate catheters are placed. Especially for radiofrequency ablation of the left atrium, considerable manipulation of the tip of the catheter across the atrial septum is typically required. The risk associated with the manipulation of the catheter tip in the left atrium is inadvertent retraction of the sheath through the septum and back into the right atrium. Typically, because of the risk to the patient engendered by transseptal puncture and because of the common use of an anticoagulant to reduce the possibility of embolism after catheter access into the left atrium, it is desirable that only one transseptal puncture be attempted during the procedure. Only infrequently will the surgeon attempt a second transseptal approach during a single procedure.

Moreover, where retraction of the sheath tip back through the atrial septum is undetected, further manipulation under the mistaken belief of positioning in the left atrium presents other risks to nearby tissue. Especially for radiofrequency ablation of areas of the left atrium relatively near the atrial septum, the risk of inadvertent retraction of the sheath into the right atrium is heightened.

Following previously known procedures, the problem of inadvertent withdrawal of the catheter tip from the left atrium, through the atrial septum, and back into the right atrium remains a risk.

It is an objective of the present invention to provide a retaining means for retaining the distal tip of a sheath which has been placed through a septum, such as the interatrial septum, across the septum, in the left atrium during left heart procedures.

It is another objective of the present invention to provide retaining means for transseptal catheterization which is selectively deployable and retractable.

It is yet a further objective of the present invention to provide a method of transseptal catheterization, with subsequent manipulation of instruments in the left atrium, which assures proper positioning of the distal tip of the sheath through which those instruments are passed, within the left atrium, while avoiding inadvertent withdrawal of the sheath tip back through the septum.

SUMMARY OF THE INVENTION

The invention comprises retaining apparatus for transseptal catheterization and a procedure for the use of same. The retaining apparatus is a selectively deployable retaining means disposed at or proximal to the tip of the transseptal catheter assembly, including a sheath and dilator which is placed across the interatrial septum, into the left atrium. The retaining means is configured to cooperate with the distal portion of the sheath to present a uniform cylindrical circumferential periphery when the retaining means is undeployed and to present a shape generally transverse to the longitudinal axis of the sheath when deployed.

In a preferred embodiment, the retaining means is a retaining balloon which, upon inflation, presents a relatively flat, disk-like shape to comprise a physical barrier for preventing inadvertent retraction of the distal tip of the sheath from the left atrium during subsequent portions of the catheterization procedure.

The transseptal catheterization procedure of the present invention includes the steps of placing the distal tip of the transseptal sheath across the interatrial septum, deploying the retaining means for retaining the distal tip within the left atrium, completing the left heart portion of the catheterization procedure, retracting the selectively deployable retaining means, and withdrawing the distal tip from the left atrium and completing the procedure.

The invention may be applicable for use with septums other than the interatrial septum.

BRIEF DESCRIPTION OF THE DRAWINGS

FIG. 1 is a representation of a patient including a schematic depiction of the heart and showing typical right femoral vein access of a transseptal catheter assembly with the dilator tip extending beyond the sheath and through the interatrial septum of the heart;

FIG. 2A is a schematic representation of the heart in which the sheath tip has been placed against a desired location of the interatrial septum prior to penetration of the septum

DETAILED DESCRIPTION OF THE PREFERRED EMBODIMENT

As shown in the schematic representation of FIG. 1, current transseptal catheterization involves access by the transseptal catheter assembly 8, preferably through the right femoral vein, with the tip of a sheath 10 passing through the right atrium, and then across the interatrial septum, into the left atrium.

Figure 2B:
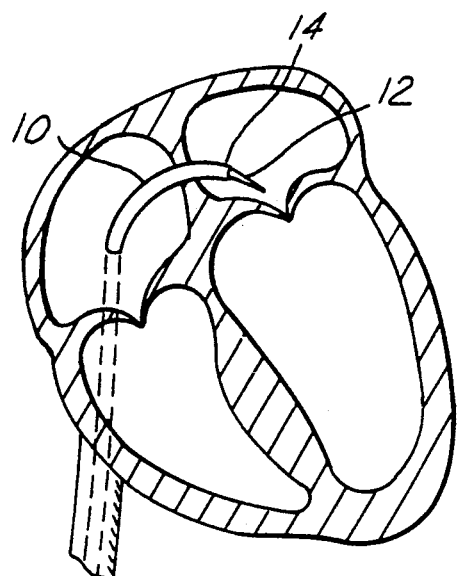
FIG. 2B shows a schematic representation of the heart with a transseptal catheter assembly which has been placed across the interatrial septum.

By a method described in greater detail below, the transseptal catheter assembly 8 of the present invention, which includes a transseptal sheath 10 and a dilator 12, is eventually placed against a septum, such as the interatrial septum, as illustrated in FIG. 2A. Following penetration of the interatrial septum with a transseptal needle, the distal tip 14 of the transseptal sheath 10, along with the tip of the dilator 12, is passed through the septum and into the left atrium, as illustrated in FIG. 2B.

Figure 2C:
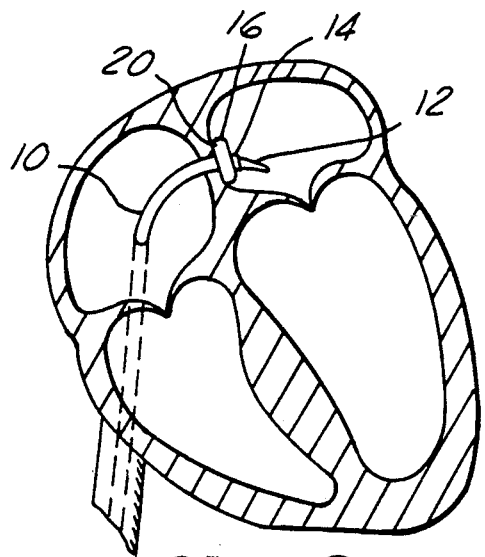
FIG. 2C is a schematic diagram of the heart in which the transseptal sheath has its retaining means selectively deployed in order to securely position the tip of the transseptal sheath within the left atrium of the heart.

FIG. 2C shows the retaining means 16 of the present invention which is selectively deployable to retain the distal tip 14 of sheath 10 within the left atrium of the heart while subsequent instruments are passed through sheath 10 to accomplish further left heart procedures. The retaining means 16 may preferably be disposed at the distal tip 14 of sheath 10, but there may be uses when it is convenient to have retaining means 16 disposed on sheath 10 spaced apart from distal tip 14.

Figure 3:
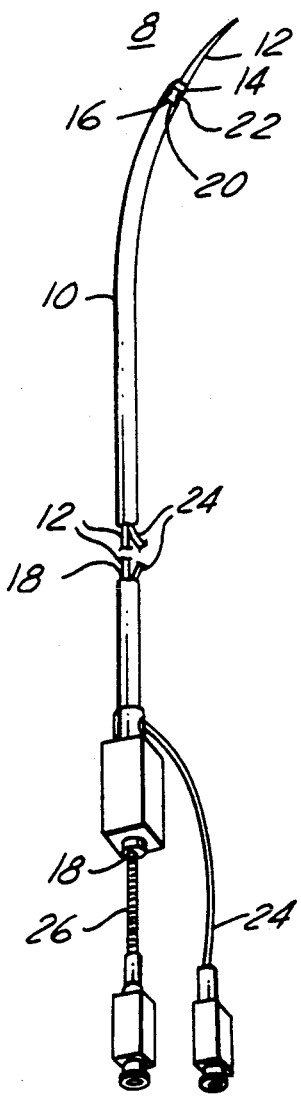
FIG. 3 is a fragmented illustration of the transseptal catheter assembly of the present invention.

As shown in FIG. 3, sheath 10 of the present invention has a main lumen 18 through which instruments such as dilator 12 may pass. FIG. 3 also shows that the transseptal sheath 10 of the present invention may also be provided with markings 26 at the proximal end nearest to the physician or operator positioned to indicate the direction of the preset curve at a distal portion of the sheath 10, and to indicate the distance between the distal tip 14 of sheath 10 and the distal tip of dilator 12.

Figure 4:
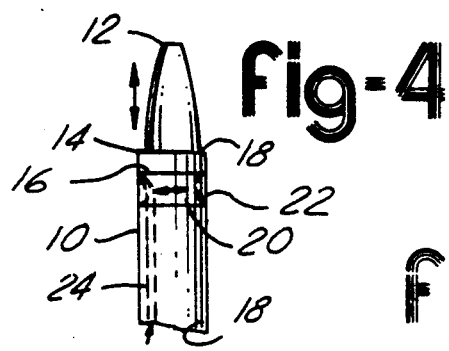
FIG. 4 is a side view of a portion of the transseptal catheter assembly of the present invention showing the retaining means prior to selective deployment.

In a preferred embodiment of the present invention, a retaininq means 16 comprises a retaining balloon 20. As shown in FIG. 4, retaining balloon 20 is preferably disposed within a concave portion 22 of sheath 10 located at or proximal the distal tip 14. The sheath 10, retaining balloon 20, and concave portion 22 are all configured such that the sheath and balloon present a uniform, columnar circumferential periphery of the sheath when the retaining balloon 20 is in its undeployed, deflated position. Alternatively, sheath 10 may be formed without a concave portion 22, in which case retaining balloon 20 is configured so that it presents as small a bulk as possible upon the outer periphery of sheath 10, when retaining balloon 20 is undeployed, to minimize the effort needed to advance sheath 10 through the septum.

Figure 5:
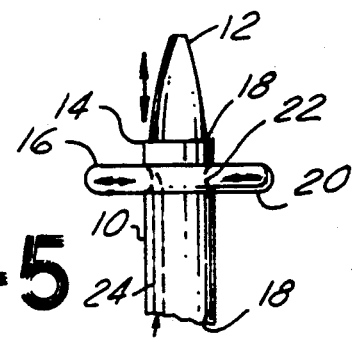
FIG. 5 shows a side view of a portion of the transseptal catheter assembly of the present invention in which the retaining means has been selectively deployed.

Retaining means 16, which in this preferred embodiment consists of retaining balloon 20, is selectively deployable once the distal tip 14 and concave portion 22 of sheath 10 have been advanced across the interatrial septum and into the left atrium of the heart. In the preferred embodiment as illustrated in FIG. 5, when retaining balloon 20 is selectively deployed, by inflation, it assumes a relatively flat, disk-like shape generally transverse to the longitudinal axis of sheath 10. As shown in FIG. 2C, the retaining balloon 20 extends transversely from sheath 10 to an extent sufficient to ensure that the distal tip 14 of sheath 10 is retained within the left atrium.

Retaining balloon 20 is selectively deployed by inflation with a fluid which passes through a balloon lumen 24, as shown in FIG. 4. It should be noted that while FIG. 4 shows balloon lumen 24 to be located within sheath 10 in adjacent and substantially parallel relationship to main lumen 18, other embodiments of sheath 10 of the present invention may configure balloon lumen 24 to be outside and surrounding main lumen 18, perhaps in concentric relationship therewith or within the main lumen.

It should be noted that while any physiologically compatible fluid is capable of passing through balloon lumen 24 to serve as the medium which inflates selectively deployable retaining balloon 20, present medical practice provides that such inflating fluid is preferably a biologically inert fluid. Examples of such preferable inflation fluids include carbon dioxide gas, contrast agent, or saline or dextrose solution or a combination of these; other gases such as air may serve to inflate retaining balloon 20 but present unnecessary risk of embolism in the unlikely event of rupture of retaining balloon 20 or of balloon lumen 24.

As appreciated by those skilled in the art, the proximal terminus of sheath 10 adjacent to the operator may be provided with apparatus similar to that currently used with transseptal catheter assemblies. Thus, the proximal terminus may be provided with a connector sleeve to facilitate connection of various devices to sheath 10, such as pressure measuring apparatus. Likewise, the proximal terminus of sheath 10 may be provided with one or more side arms to allow multiple connections to additional apparatuses. Finally, the proximal terminus of sheath 10 may simply be an open end, with or without closure means, such as a protective, penetrable membrane or the like.

As shown in FIG. 3, the proximal terminus of the catheter assembly may be provided with additional measuring or locating indicia 26 to assist the operator in locating the position of the distal tip of instruments such as dilator 12, relative to the distal tip 14 of sheath 10. As appreciated by those skilled in the art, such measuring or locating indicia 26 may be as simple as markings placed at the proximal terminus of either or both of the sheath 10 and dilator 12 or within the sheath. The markings may also be positioned specifically on the periphery to accurately indicate the direction of the preset curvature generally at the distal end of sheath 10. Alternatively of course, sheath 10 of the present invention may be formed without a preset curved distal portion if so desired.

Alternative embodiments of transseptal sheath 10 of the present invention provide retaining means 16 which comprise a plurality of selectively deployable ribs circumferentially spaced about the periphery of sheath 10 at or near distal tip 14. Again, where retaining means 16 comprise such selectively deployable ribs, the ribs are preferably disposed within a concave portion 22 of the outer periphery of sheath 10. Sheath 10, concave portion 22, and the ribs comprising retaining means 16 thus are configured such that the sheath and ribs present a uniform, columnar circumferential periphery when the ribs of retaining means 16 are not selectively deployed.

In such an alternative embodiment, balloon lumen 24 is replaced by a control means lumen 24a through which control means serve to control the selective deployment of the ribs. In one alternative embodiment, the control means lumen 24a may be in coaxial relationship with and surrounding main lumen 18, and may house a circumferential control sleeve which is longitudinally advanceable within sheath 10. Upon such longitudinal advancement within the sheath, the control sleeve would bear against the ribs comprising retaining means 16 to cause their selective deployment to a position in which the ribs are generally transverse to the longitudinal axis of sheath 10. In such transverse position, the ribs comprising retaining means 16 would serve to retain distal tip 14 of sheath 10 within the left atrium. Likewise, retraction of the control sleeve would serve to control the retraction of the ribs comprising retaining means 16 into an undeployed position.

In this alternative embodiment, ribs comprising retaining means 16 may also be provided with a biasing means to bias the ribs into the undeployed position. Thus, at any time in which the control sleeve is not longitudinally advanced to counteract the biasing means, such biasing means serves to urge the ribs to assume the undeployed position. In that position, the sheath and ribs present a uniform columnar circumferential periphery which does not affect the ability of the distal tip 14 of sheath 10 to advance or retract within the patient's body.

As will be readily appreciated by those skilled in the art, in alternative embodiments, retaining means 16 may be of a configuration other than one which would be characterized as ribs. Other selectively deployable retaining means 16 of alternative configurations may be used so long as retaining means 16 provides a physical barrier generally transverse to the axis of sheath 10. The barrier serves to prevent the unintentional withdrawal of the distal tip 14 of sheath 10 from the left atrium and through the interatrial septum.

Likewise, those skilled in the art will realize that alternative control means to control the selective deployment and retraction of retaining means 16 may also serve. Such alternative configurations may include, without limitation, rotation of such control means in a first direction relative to sheath 10 to control deployment of retaining means 16. Rotation of the control means in the opposite direction controls retraction of the retaining means 16. It is anticipated that in such alternative embodiments, the control means will interact with the retaining means 16 through a control means lumen 24a analogous to balloon lumen 24 in the preferred embodiment described above.

In use, the method of the present invention provides a procedure for transseptal catheterization which includes the steps of placing the distal tip of a transseptal sheath of the configuration described above, across the interatrial septum, and then deploying the distal tip 14 within the left atrium. Subsequently, the remaining left heart portion of the catheterization procedure is completed. This left heart portion may include any procedure for which catheter access to or through the left atrium has been accomplished. After completion of the left heart portion of the catheterization procedure, the retaining means is retracted and the distal tip 14 of sheath 10 is withdrawn from the left atrium. The catheterization procedure is then completed. As will be appreciated from a reading of the description above, the step of deploying the retaining means secures the distal tip 14 of sheath 10 within the left atrium during subsequent portions of the procedure.

In combination with the present practice for transseptal catheterization, the method of the present invention for transseptal catheterization includes the following steps. First, the operator punctures a vein with a hollow needle. In present practice, the preferred vein is the right femoral vein, although access from the left femoral vein is also possible. Furthermore, it would also be theoretically possible to accomplish the procedure through any other vein of the body of suitable internal diameter and the present invention would also subsume access through other veins.

Next, a spring guide wire is placed through the needle into the vein and the needle is subsequently removed. A sheath 10 of the present invention with an inner dilator positioned in main lumen 1B is then introduced over the guide wire. Subsequently, sheath 10 and inner dilator 12, in combination with the guide wire, are advanced through the vein to the superior vena cava. The guide wire is then removed.

When the sheath 10 and dilator 12 are in the superior vena cava and the guide wire has been removed, a transseptal needle, with a stylet placed within the hollow lumen of the transseptal needle, is advanced through the dilator 12 and sheath 10. The transseptal needle is advanced with the stylet in place to prevent trauma to the catheter from the transseptal needle at this stage. When the transseptal needle has been advanced to a point that the stylet tip is just inside the distal tip of the sheath 10 and dilator 12, a position previously noted by the operator, the stylet is withdrawn from the transseptal needle, and the needle advanced to a point just inside the distal tip of dilator 12.

The remaining combination of the sheath 10 with dilator within main lumen 18, and the transseptal needle just within the tip of the dilator, is then drawn back from the superior vena cava until a point when the preset curve at the distal region of sheath 10 and dilator 12 causes the tip of the sheath-dilator-transseptal needle combination to enter the right atrium.

It will be appreciated by those skilled in the art that the step of advancing this combination into the superior vena cava prior to placing them into the right atrium is primarily to facilitate locating the tip of the combination relative to a known landmark of the heart. It is possible to eliminate the step of advancing these instruments into the superior vena cava before drawing them back to enter the right atrium, although this is not current preferred medical practice.

With the sheath-dilator-transseptal needle combination now within the right atrium, the tip of this combination is positioned against a desired location of the interatrial septum. The physician is assisted in this step, as in the entire procedure, by visualization via fluoroscopy or other visualization techniques. To assist in such visualization, the distal tip 14 of sheath 10 and the distal tip of dilator 12 may be provided with a radiopaque material. Likewise, some physicians find it preferable to infuse a radiopaque dye through the transseptal needle at various stages of the procedure to assist in visualization.

After the tip of the sheath-dilator-transseptal needle combination has been placed in the desired location against the interatrial septum, the transseptal needle is abruptly advanced to accomplish a quick puncture of the interatrial septum. Immediately after the puncture, the preferred medical technique is to confirm the presence of the tip of the transseptal needle within the left atrium. Confirmation of such location of the tip of the transseptal needle may be accomplished by monitoring the pressure sensed through the transseptal needle lumen to ensure that the measured pressure is within the expected range and has a waveform configuration typical of left atrial pressure. Alternatively, proper position within the left atrium may be confirmed by analysis of oxygen saturation level of the blood drawn through the transseptal needle; i.e., aspirating fully oxygenated blood. Finally, visualization through fluoroscopy alone, or in combination with the use of dye, may also serve to confirm the presence of the tip of the transseptal needle in the left atrium.

Where any of these confirmation techniques indicate that the transseptal needle tip has not entered the left atrium, the operator must promptly analyze and deal with the consequences of improper placement and puncture of inappropriate tissue. While the step of confirming the appropriate presence of the tip of the transseptal needle within the left atrium is thus currently within prudent medical practice, such a step is not essential to the physical steps required in this procedure.

After placing the transseptal needle tip within the left atrium, the tip of the dilator 12 and sheath 10 are next advanced through the septum and into the left atrium. Typically, care is taken to ensure that, at the same time of advancing the dilator and sheath tip into the left atrium, the tip of the transseptal needle is not injudiciously advanced. When the tip of dilator 12 appears to have entered the left atrium, the transseptal needle is withdrawn. The sheath 10 is then advanced into the left atrium, either by advancing the sheath 10 alone over the dilator 12 or by advancing the sheath and dilator in combination. The dilator 12 is then withdrawn from sheath 10 when the latter has been advanced into the left atrium, thus leaving main lumen 18 of sheath 10 as a clear pathway to advancing further instruments into the left atrium.

In accordance with the method of the present invention, after the distal tip 14 of sheath 10 has been placed within the left atrium, retaining means 16 may be deployed to retain the distal tip 14 within the left atrium. As this step of deploying retaining means 16 may be effectuated any time after distal tip 14 has been placed within the left atrium, the step of deploying the retaining means may be accomplished either before or after the transseptal needle and dilator 12 are withdrawn from the left atrium.

Where the procedure is being accomplished with a sheath 10 of the preferred embodiment, the step of selectively deploying retaining means 16 comprises the step of introducing an inflating fluid into balloon lumen 24 until the retaining balloon 20 inflates to a point where it projects sufficiently in a direction transverse to the longitudinal action of sheath 10 to accomplish its retaining function.

Where the procedure is being accomplished with an alternative embodiment of sheath 10 of the present invention, the operator uses appropriate actuating means to selectively deploy the ribs or alternate forms which comprise retaining means 16.

The next step in the method of the present invention is drawing back sheath 10 until retaining means 16 bears against the interatrial septum. This step serves to secure the position of distal tip 14 of sheath 10 to a known location, namely the known distance between the distal tip 14 and retaining means 16. As retaining means 16 also bears against the septum, the operator thus knows that the distal tip 14 is a certain known distance from the septum.

With the sheath 10 of the present invention providing access to the left atrium and with retaining means 16 being deployed and bearing against the interatrial septum, the remaining transseptal portion of the catheterization procedure may be accomplished. Where such remaining transseptal, i.e., left heart, portion of the catheterization procedure is radiofrequency ablation, such subsequent left heart portion may include mapping of the areas of the left heart of interest, with subsequent electrode positioning and radiofrequency application to ablate electrical pathways. The deployment of retaining means 16 of sheath 10 is expected to contribute significantly to stability of electrode positioning for such a procedure, to preventing inadvertent withdrawal of sheath 10, and to positioning the tip of sheath 10 flush with the septum to allow easier access to pathways within or near the septum.

The remaining left heart portion of the catheterization procedure may also be diagnostic, as in monitoring left atrial pressure during subsequent procedures affecting the heart or other areas of the patient's body. The remaining left heart portion may also be therapeutic, such as valvuloplasty of areas of the left heart, such as the mitral valve.

Once the remaining left heart portion of the catheterization procedure is completed, selectively deployable retaining means 16 may be retracted and the distal tip 14 of sheath 10 may be withdrawn from the left atrium. The remaining closing portion of the catheterization procedure may then be completed.

It should be noted that the retaining means 16 of the transseptal sheath 10 disclosed herein is expected to significantly reduce the number of times in which a procedure in the left heart must be interrupted before completion, with possible subsequent attempts at a later date. The necessity to interrupt the procedure, and attendant needs to postpone a second attempt to a later date, if ever, arises in the following manner. In present medical practice, once left atrial access has been achieved, as by transseptal approach, an anticoagulant is routinely administered to the patient to reduce the possibility of embolism as a result of the invasive procedure. Thus, where the distal tip of a transseptal sheath is inadvertently withdrawn from the left atrium during subsequent instrument manipulation during the left heart portion of the catheterization, current prudent medical practice contraindicates an immediate subsequent second attempt at transseptal penetration. Such immediate second transseptal penetration is to be avoided because of the increased severity of adverse consequences if inadvertent puncture of surrounding tissue is made due to a mistaken belief that the transseptal needle has been correctly positioned against the septum. Obviously, the severity of the consequences of such inadvertent puncture of surrounding tissue is heightened by virtue of the presence of the anticoagulant in the patient.

It is thus seen that the present invention, by providing a retaining means 16 to ensure that distal tip 14 of sheath 10 is retained in the left atrium during the subsequent left heart portion of the catheterization, ensures against inadvertent withdrawal of the sheath 10 from the left atrium, thus reducing the number of incomplete procedures and the number of subsequent additional procedures to complete the intended task. Further, the ability to position the tip of sheath 10 flush with the septum may facilitate free manipulation of other instruments introduced through main lumen 18.

Those skilled in the art will appreciate that, while the invention has been described with regard to transseptal catheterization across the interatrial septum, it may be used to advantage in catheterizations across other septums within the human body as well.

It will be understood by those skilled in the art that the foregoing description of the transseptal sheath and method of using the same are capable of alternative embodiments which are still within the scope of the present invention, which is to be limited only by the following claims.

What is claimed is:

1. A cardiac transseptal sheath for a transseptal catheterization procedure which involves positioning the sheath across a septum between a right atrium and a left atrium of a heart, said sheath having a main lumen and having selectively deployable retaining means for retaining a distal tip of said sheath in relation to the septum during the catheterization procedure, said sheath having a curved distal end to facilitate emplacement in the left atrium and passage therethrough of devices for diagnostic or therapeutic purposes.

2. The sheath of claim 1 wherein said retaining means comprises a soft, compliant, selectively inflatable balloon disposed at the distal tip of said sheath.

3. The sheath of claim 2 further comprising a balloon lumen for passing an inflating fluid into said inflatable balloon.

4. The sheath of claim 3 wherein said balloon lumen and said main lumen are adjacent and substantially parallel to each other within said sheath.

5. The sheath of claim 3 wherein said balloon lumen is concentric with and surrounds said main lumen.

6. The sheath of claim 3 wherein said balloon lumen is within said main lumen.

7. The sheath of claim 3 wherein said sheath has a circumferentially concave portion disposed at said tip, said balloon being disposed within said concave area and being configured so that said sheath and balloon present a uniform, cylindrical circumferential periphery when said balloon is deflated.

8. The sheath of claim 1 wherein said retaining means comprises a selectively inflatable balloon disposed on the sheath spaced apart from said distal tip.

9. The sheath of claim 8 further comprising a balloon lumen for passing an inflating fluid into said inflatable balloon.

10. The sheath of claim 9 wherein said balloon lumen and said main lumen are adjacent and substantially parallel to each other within said sheath.

11. The sheath of claim 9 wherein said balloon lumen is concentric with and surrounds said main lumen.

12. The sheath of claim 9 wherein said balloon lumen is within said main lumen.

13. The sheath of claim 9 wherein said sheath has a circumferentially concave portion disposed on the sheath spaced apart from said distal tip and said balloon is disposed within said concave area and is configured so that said sheath and balloon present a uniform, cylindrical circumferential periphery when said balloon is deflated.

14. The sheath of claim 1 wherein said retaining means comprises a plurality of selectively deployable ribs circumferentially spaced about the periphery of said sheath and disposed proximate the distal tip of said sheath.

15. The sheath of claim 14 further comprising control means for controlling deployment of said ribs, said control means extending longitudinally with said sheath.

16. The sheath of claim 15 wherein said control means comprises a longitudinally advanceable circumferential sleeve disposed within said sheath which, upon advancement, engages and deploys said ribs.

17. The sheath of claim 16 wherein retraction of said longitudinally advanceable sleeve retracts said ribs.

18. The sheath of claim 14 further comprising biasing means to retract said ribs.

19. A procedure for cardiac transseptal catheterization comprising the steps of:

a) placing a curved distal tip of a transseptal sheath across the interatrial septum;
b) deploying retaining means for retaining said distal tip in relation to the septum, whereby deployment of said retaining means secures said distal tip in relation to the septum during subsequent portions of the procedure;
c) comprising a transseptal portion of the catheterization procedure;
d) retracting said retaining means; and
e) withdrawing said distal tip from the septum and completing the catheterization procedure.

20. The procedure of claim 19 wherein the step of placing the distal tip of the transseptal sheath across the interatrial septum further comprises the steps of:
a) advancing a curved sheath-dilator-transseptal needle combination into the right atrium;
b) placing a tip of said sheath-dilator-transseptal needle combination against a desired location of the interatrial septum;
c) puncturing said interatrial septum with a transseptal needle of the combination;
d) advancing the tip of the dilator and sheath through the septum and into the left atrium; and
e) withdrawing said transept al needle and dilator.

21. The procedure of claim 20 comprising the further steps of:
a) percutaneously puncturing a vein with a hollow needle;
b) placing a spring guide wire within the needle into the vein;
c) removing said needle;
d) introducing a sheath with an inner dilator over said guidewire;
e) advancing said sheath and dilator into the vein and towards the heart;
f) removing said guidewire;
g) advancing a stylet and said transseptal needle through said dilator and sheath;
h) withdrawing said stylet from said transseptal needle.

22. The procedure of claim 19 wherein said retaining means comprises a soft, compliant, selectively inflatable balloon and said sheath comprises a balloon lumen, said step of deploying said retaining means further comprising the step of inflating said balloon by passing an inflating fluid through said balloon lumen.

23. A procedure for cardiac transseptal catheterization comprising the steps of:
a) percutaneously puncturing a vein with a hollow needle;
b) placing a spring guidewire within the needle into the vein;
c) removing said needle;
d) introducing a curved sheath with inner dilator over said guidewire;
e) advancing said sheath and dilator into the vein and into the superior vena cava;
f) removing said guidewire;
g) advancing a stylet and said transseptal needle through said dilator and sheath;
h) withdrawing said stylet from said transseptal needle;
i) drawing back said transseptal needle, said dilator and said sheath until said transseptal needle, dilator and sheath enter the right atrium;
j) placing the tip of a combination of said sheath, dilator and transseptal needle against a desired location of the interatrial septum;
k) puncturing said interatrial septum with said transseptal needle;
l) advancing the tip of the dilator and sheath through the septum and into the left atrium;
m) withdrawing said transseptal needle and dilator;
n) deploying a soft, compliant retaining means for retaining the sheath tip within the left atrium;
o) drawing back said sheath until said retaining means bears against the septum;
p) continuing with the remaining left heart portion of the catheterization procedure;
q) retracting said retaining means;
r) withdrawing said sheath tip from the left atrium; and
s) completing the remaining portion of said catheterization procedure.

24. A procedure for cardiac transseptal catheter comprising the steps of:
a) percutaneously puncturing a femoral vein with a hollow needle;
b) placing a spring guidewire within the needle into the femoral vein;
c) removing said needle;
d) introducing a curved sheath with inner dilator over said guidewire;
e) advancing said sheath and dilator into the femoral vein and advancing said sheath and dilator to the superior vena cava;
f) removing said guidewire;
g) advancing a stylet and said transseptal needle through said dilator and sheath;
h) withdrawing said stylet from said transseptal needle;
i) drawing back said transseptal needle, said dilator and said sheath until said transseptal needle, dilator and sheath enter the right
j) placing the tip of said sheath-dilator-transseptal needle combination against a desired location of the interatrial septum;
k) puncturing said interatrial septum with said transseptal needle;
l) confirming the presence of the transseptal needle in the left atrium;
m) advancing the tip of the dilator and sheath through the septum and into the left atrium;
n) withdrawing said transseptal needle and dilator;
o) deploying a soft, compliant retaining means for retaining the sheath tip within the left atrium;
p) drawing back said sheath until said retaining means bears against the septum;
q) continuing with the remaining left heart portion of the catheterization procedure;
r) retracting said retaining means;
s) withdrawing said sheath tip from the left atrium; and
t) completing the remaining portion of said catheterization procedure.

* * * * *